(12) United States Patent
Chang et al.

(10) Patent No.: US 11,679,272 B2
(45) Date of Patent: *Jun. 20, 2023

(54) PROCESS FOR SAFELY PROVIDING RETINAL PHOTOTHERAPY BASED ON DETERMINATION OF RPE MELANIN LEVELS

(71) Applicant: Ojai Retinal Technology, LLC, Ojai, CA (US)

(72) Inventors: David B. Chang, Tustin, CA (US); Jeffrey K. Luttrull, Ojai, CA (US)

(73) Assignee: Ojai Retinal Technology, LLC, Los Angeles, CA (US)

( * ) Notice: Subject to any disclaimer, the term of this patent is extended or adjusted under 35 U.S.C. 154(b) by 535 days.

This patent is subject to a terminal disclaimer.

(21) Appl. No.: 16/540,886

(22) Filed: Aug. 14, 2019

(65) Prior Publication Data

US 2019/0366121 A1    Dec. 5, 2019

Related U.S. Application Data

(63) Continuation of application No. 16/241,812, filed on Jan. 7, 2019, now Pat. No. 10,434,330, which is a
(Continued)

(51) Int. Cl.
*A61B 3/10* (2006.01)
*A61N 5/06* (2006.01)

(52) U.S. Cl.
CPC ............ *A61N 5/0622* (2013.01); *A61B 3/102* (2013.01); *A61N 2005/0628* (2013.01)

(58) Field of Classification Search
CPC ......... A61B 3/102; A61B 3/12; A61B 3/0025; A61F 9/008; A61N 5/0622; A61N 2005/0628; G01B 9/02091
See application file for complete search history.

(56) References Cited

U.S. PATENT DOCUMENTS 6,276,798 B1   8/2001   Gil et al.
6,540,391 B2   4/2003   Lanzetta et al.
(Continued)

FOREIGN PATENT DOCUMENTS

WO   2016/075868 A1   5/2016

OTHER PUBLICATIONS

Zhang et al. In vivo Optical Coherence Tomography of Light-Driven Melanosome Translocation in Retinal Pigment Epithelium, Sep. 12, 2013, Scientific Reports 3: 2644 (Year: 2013).*
(Continued)

*Primary Examiner* — Ephrem Z Mebrahtu
(74) *Attorney, Agent, or Firm* — Kelly & Kelley, LLP

(57) ABSTRACT

A process for safely providing retinal phototherapy includes generating an interferometric signal or pattern by applying a near infrared light beam to a retinal pigment epithelium of a retina of an eye. A level or concentration of melanin within the retinal pigment epithelium of the retina is compared to a normal level or concentration using the detected interferometric signal or pattern. One or more treatment parameters of the retinal phototherapy is adjusted if the level or concentration of melanin in the retinal pigment epithelium of the eye exceeds the normal level or concentration by a predetermined amount.

28 Claims, 10 Drawing Sheets

Related U.S. Application Data continuation-in-part of application No. 16/203,970, filed on Nov. 29, 2018, now Pat. No. 10,952,899, and a continuation-in-part of application No. 15/818,216, filed on Nov. 20, 2017, now Pat. No. 10,194,798.

(56) References Cited

U.S. PATENT DOCUMENTS

| | | | |
|---|---|---|---|
| 7,039,452 | B2 | 5/2006 | McClane et al. |
| 7,118,217 | B2 | 10/2006 | Kardon et al. |
| 7,467,870 | B2 | 12/2008 | van de Kraats et al. |
| 8,308,299 | B2 | 11/2012 | Ramella-Roman et al. |
| 8,326,405 | B2 | 12/2012 | Gellermann et al. |
| 8,485,664 | B2 | 7/2013 | Rowe |
| 8,807,751 | B2 | 8/2014 | Kahn et al. |
| 9,010,935 | B2 | 4/2015 | Cui et al. |
| 9,173,562 | B2 | 11/2015 | Sardar et al. |
| 9,332,905 | B1 | 5/2016 | Sims |
| 2007/0213693 | A1* | 9/2007 | Plunkett ............ A61F 9/008 606/6 |
| 2010/0085537 | A1 | 4/2010 | Ramella-Roman et al. |
| 2011/0261321 | A1 | 10/2011 | Ramella-Ramon et al. |
| 2012/0092619 | A1 | 4/2012 | Rowe |
| 2013/0028484 | A1* | 1/2013 | Wada ............... A61B 3/12 382/106 |
| 2013/0128227 | A1 | 5/2013 | Cui et al. |
| 2017/0035291 | A1* | 2/2017 | Jiao ............ A61B 3/0025 |
| 2018/0263695 | A1* | 9/2018 | Kim ............ A61N 5/06 |
| 2019/0151146 | A1* | 5/2019 | Kim ............ A61F 9/00814 |

OTHER PUBLICATIONS

R.R. Anderson and J.A. Parrish (1981) The optics of human skin. J. Invest. Dermatol 77, 13-19.
S. Asano & G. Yamamoto (1975), Light scattering by a spheroidal particle. AppliedOptics 14: 29-50.
R. Bingruber (1984) Choroidal circulation and heat convection at the fundus of the eye: implications for laser coagulation and the stabilization of retinal temperature. Laser Applications in Medicine and Biology, Springer, 277-361.
R.A. Bone, B. Brener, J.C. Gibert (2007) Macular pigment, photopigments, and melanin: distribution in young subjects determined by four-wavelength reflectometry. Vis. Res. 47, 3259-3268.
T. Burgoyne, M.N. O'Connor, M.C. Seabra,D.F. Cutler, C.E. Futter (2015) Regulation of melanosome number, shape, and movement in the zebrafish retinal pigment epithelium by OA1 and PMEL. J.Cell Sci.128, 1400-1407.
Chemspider: Melanin (2015) Structure, properties, spectra, suppliers and links for: Melanin, 8049-97-6, www.chemspider.com/Chemical-Structure.4884931.html.
T.C. Chen, C. Chuang, J. Cao, V. Ball, D. Ruch, M.J. Buehler (2014) Excitonic effects from geometric order and disorder explain broadband optical absorption in eumelanin. Nat. Commun. 5.3859 doi: 10.1038/ncomms4859.
A.J. Cox, A.J. DeWeerd, & J. Linden(2002) An experiment to measure Mie and Rayleigh scattering cross sections. Am. J. Phys. 70, 620-625.
A.E. Elsner, S.A. Burns, J.J. Weiter, F.C. Delori (1996) Infrared imaging of sub-retinal structures in the human ocular fundus. Vision Res. 36, 191-205.

V.P. Gabel, R. Birngruber, F. Hillenkamp(1978) Visible and near infrared light absorption in pigment epithelium and choroid in Kyoto, Sh8mizu and K.Osterhuis (Eds.) XXIII Concililium Ophth. (Excerpta Medica)invest. Ophth. 1, 340 Amsterdam: Elsevier.
W.J. Geeraets et al (1962) The relative absorption of thermal energy in retina and choroid.
R.D. Glickman, J.M. Gallas, S.L. Jacques, B.A. Rockwell, D.K. Sardar(2001)Physical and photochemical properties of ocular melanin. Proc. of SPEI 4241,112-123.
M. Hammer, D. Schweitzer, E. Thamm, A. Kolb, J. Strobel (2001) Scattering properties of the retina and the choroids determined from OCT-A-scans. Intl. Ophthalmol. 23, 291-295.
S. Jacques (1998) Melanosome absorption coefficient. Oregon Medical Laser Center, http://omic.org.
M. Jastrzebska, A. Kocot, J.K. Vij, J. Zalewska-Rejdak, T. Witecki (2002) Dielectric studies on charge hopping in melanin polymer. J. Molec. Struct. 606, 205-210.
I.T. Kim & J.B. Choi(1998) Melanosomes of retinal pigment epithelium—distribution, shape, and acid phosphatase activity. Korean J. Ophthalmol. 12, 85-91.
P. Kubelka & F. Munk (1931) Ein beitrag zur optick derfarbanstriche. Z. Tech. Phys. (Leipzig) 12, 593-601.
I.A. Menon, S. Persad, H.F. Haberman, C.J. Kunan, P.K. Basu (1982) A quantitative study of the melanins from blue and brown human eyes. Exp. Eye Res. 34, 531-537.
P. Meredith & T. Sama (2006) The physical and chemical properties of melanin. Pigment Cell Res. 19, 572-594.
A.B. Mostert, B.J. Powell, F.L. Pratt, G.R. Hanson, T. Sama, I.R. Gentle, P. Meredith (2012) Role of semiconductivity and ion transport in the electrical conduction of melanin. PNAS 109, 8943-8947.
S.J. Preece & E. Claridge (2002) Monte Carlo modelling of the spectral reflectance of the human eye. Phys. Med. Biol. 47, 2863-2877.
J. Riesz, J. Gillmore, P. Meredith (2006) Quantitative scattering of melanin solutions. Biophys. J. 90, 4137-4144.
J. Riesz (2007) The spectroscopic properties of melanin. PhD thesis, University of Queensland.
L.I. Schiff (1955) Quantum Mechanics. New York: McGraw-Hill, 169.
J. van de Kraats ,T.T.J.M. Berendschot, D. van Norren (1996) The pathways of light measured in fundus reflectometry. Vision Res. 36, 2229-2247.
V. Wang and HI. Wu (2007) Biomedical Optics: Principles and Imaging. Wiley. ISBN 978-0-471-74304-0.
J.J. Weiter, F.C. Delori, G.L. Wing, K.A. Fitch (1986) Retinal pigment epithelial lipofuscin and melanin and choroidal melanin in human eyes. Inv. Ophth. Vis. Sci. 27, 145-152.
A.M. Zysk, F.T. Nguyen, A.L. Oldenburg, D.L Marks, S.A. Boopart (2007) Optical coherence tomography: review of clinical development from bench to bedside. J. Biomed. Optics 12, 051403.
International Search Report for the International application No. PCT/US2017/062834, dated Feb. 12, 2018.
Jay Chhablani, MD et al., "Restorative retinal laser therapy: Present state and future directions", survey of ophthalmology 63 (2018) 307-328.
Jeffrey K. Luttrull et al. "Functionally Guided Retinal Protective Therapy for Dry Age-Related Macular and Inherited Retinal Degenerations: A Pilot Study", Investigative Ophthalmology & Visual Science, Jan. 2016, p. 265-275, vol. 57 No. 1.
Forrest W. Nutter Jr., "Weber-Fechner Law", Iowa State University Digital Repository, 2010.

* cited by examiner

PROCESS FOR SAFELY PROVIDING RETINAL PHOTOTHERAPY BASED ON DETERMINATION OF RPE MELANIN LEVELS

RELATED APPLICATION

This application is a continuation of U.S. application Ser. No. 16/241,812, filed Jan. 7, 2019, which is a continuation-in-part of U.S. application Ser. No. 16/203,970, filed Nov. 29, 2018, which is a continuation-in-part of U.S. application Ser. No. 15/818,216, filed Nov. 20, 2017.

FIELD OF THE INVENTION

The present invention generally relates to a process for safely providing retinal phototherapy. More particularly, the present invention is directed to a process for safely providing retinal phototherapy by adjusting treatment parameters of the retinal phototherapy based on a determination of an elevated melanin content of the retinal pigment epithelium (RPE).

BACKGROUND OF THE INVENTION

The importance of macular pigment to the health of the eye has prompted development and interest in methods for measuring its density or concentration in the retina. Prior systems and methods, however, have either been based upon equipment which is not commonly available, is time consuming, or complicated and expensive.

With reference now to FIG. 1, a diagrammatic view of an eye, generally referred to by the reference number 10, is shown. The eye 10 includes a cornea 12 which is a transparent front part of the eye that covers the iris and pupil 14 which is the variable-size black circular or slit-shaped opening in the center of the iris that regulates the amount of light that enters the eye. The lens 16 is a transparent biconvex structure in the eye that, along with the cornea 12, helps to refract light to be focused on the retina 18. The retina is a thin layer of neural cells that line the back of the eyeball which captures light and transforms it into electrical signals for the brain. It has many blood vessels 20 to nourish it. The fovea and macular region, referred to by the reference number 22, is a portion of the eye used for color vision and fine detail vision. The retinal pigmented epithelium (RPE) 24 is the pigmented cell layer just outside the neurosensory retina 18 that nourishes the retinal visual cells. It is firmly attached to an underlying choroid 26 which is a vascular layer of the eye 10 lined between the retina 18 and the sclera. The choroid 26 provides oxygen and nourishment to the outer layers of the retina 18.

Many diseases of the eye are related to the retina and there have been developed methodologies to treat such diseases and conditions. Some forms of phototherapy, such as photostimulation and photocoagulation, rely upon heating of the retinal tissue to create their therapeutic effects. Excessive heating can damage or even destroy retinal tissue, which in some treatment methodologies is intentional but in others is avoided. It has been found that abnormal levels of pigmentation, particularly levels or concentrations of melanin within the RPE, can cause unanticipated and excessive heat during such treatments and potentially damage the retinal tissue.

Melanin in the eye has many important functions which are not yet completely understood. Melanin in the eye provides protection to the eye by absorbing harmful ultraviolet radiation. Melanin promotes visual acuity by scattering stray light away from the rods and cones and absorbing light reflected from the back of the eye. Melanin also serves as an antioxidant to aid in the prevention of retinal diseases, such as age-related macular degeneration.

Many of these properties result from the fact that the absorption spectrum of melanin is very broad. In this respect, it is unique among pigments. Many mechanisms have been suggested for this unique behavior. As examples, the broadband absorption has been attributed to chemical heterogeneity, amorphous semiconducting, and scattering. However, it has been shown that scattering losses only account for a few percent of the broadband attenuation. There are also problems with the chemical heterogeneity and amorphous semiconducting hypothesis. Some have proposed polymeric charge hopping. Others have pointed out the importance of hydration and introducing free radicals into melanin. Yet others have suggested that melanin excitons may play a role in its broadband absorption. There does not appear to be universal agreement that any particular explanation can account for all of melanin's electrical and optical properties.

As indicated above, melanin within the eye serves many important functions. The determination of the levels or concentrations of melanin within the eye can be important to ascertain. For example, phototherapy laser treatments of eye diseases may be based on inducing temperature rises in the RPE, which activates the eye's natural repair mechanisms. In the near infrared, this results from the absorption of the infrared radiation by the melanin pigment in the RPE. Considerable melanin also exists in the choroid behind the RPE, but absorption by the choroidal melanin does not play a significant role in raising the temperature of the RPE due to the lack of diffusive heat transfer to the RPE during the relatively short treatment times and due to the convective cooling by the blood vessels in the choroid and the choriocapillaris.

In laser true subthreshold damage phototherapy treatments of eye diseases, which avoid retinal damage, the laser treatment is effective as long as the temperature rise does not exceed the order of 10° C. This temperature rise limitation determines the maximum laser energy that can be absorbed by the RPE during the treatment time. A possible concern, however, is that for laser powers that are suitable for most patients, the temperature rise can exceed the threshold for damage if the patient's RPE melanin content or concentration is abnormally too large.

Accordingly, there is a continuing need for a simple and relatively inexpensive process for determining melanin levels or concentrations within the eye, and particularly within the RPE of the eye, so that one or more treatment parameters of the retinal phototherapy treatment can be adjusted as needed to avoid damaging patient's eyes who have an abnormally large content or concentration of melanin in the RPE. The present invention fulfills these needs, and provides other related advantages

SUMMARY OF THE INVENTION

The present invention is directed to a process for safely providing retinal phototherapy by adjusting one or more treatment parameters of the retinal phototherapy if the content or concentration of melanin in the RPE of the eye is abnormally excessive.

An interferometric signal or pattern is generated by applying a near infrared light beam to a retina of an eye. Preferably, the light beam has a wavelength between 600 nm and 1000 nm and a depth resolution of the order of 3 to 10 microns. The light beam is split in to a reference beam and a sample beam which is applied to the retinal pigment epithelium of the retina of the eye.

The interferometric signal or pattern is detected. This may comprise using a photodetector to detect light reflected from the retina. An optical coherence tomography device may be used to apply the light beam to the retina and detect the interferometric signal or pattern It is determined if a level or concentration of melanin within the retinal pigment epithelium of the retina of the eye is elevated compared to a normal level or concentration using the detected interferometric signal or pattern. This may be done by calculating a ratio of abnormal retinal pigment epithelium melanin and normal retinal pigment epithelium melanin densities. This may be according to the calculation of: $[\{N\sigma_s + \mu_{backscat}\}_{RPE}/\{2N(\sigma_s+\sigma_a) + 2\mu_{backscat}\}_{RPE}]$ times $[1-\exp[-2w\{N(\sigma_s+\sigma_a)+\mu_{backscat}\}_{RPE}]]$, wherein N is the number density of the melanin aggregates that absorb and scatter the light beam; $\sigma_s$ denotes a cross section of a melanin aggregate for backwards scattering; $\sigma_a$ denotes a cross section of a melanin aggregate for absorption; and $\mu_{back\ scat}$ is a coefficient for backscattering from a structural matrix of the retina.

One or more treatment parameters of the retinal phototherapy is adjusted if the level or concentration of melanin in the retinal pigment epithelium of the eye exceeds the normal level or concentration by a predetermined amount. The one or more treatment parameters may be adjusted when the change in interferometric signal or pattern is ten percent or greater. The one or more treatment parameters may be adjusted when the level or concentration of melanin in the retinal pigment epithelium is at least three times greater than the normal level or concentration.

The adjusting step comprises adjusting at least one of a retinal spot size of a treatment light beam, a pulse train duration of the treatment light beam, a duty cycle of the treatment light beam, or a power of the treatment light beam. For example, a retinal spot size of the treatment light beam may be increased. Alternatively, or in addition, a pulse train duration of a treatment light beam may be lowered. Alternatively, or in addition, a duty cycle of a treatment light beam may be lowered. Alternatively, or in addition, a power of the treatment light beam may be lowered.

The one or more treatment parameters of the retina therapy system may be automatically adjusted when the concentration of melanin in the retinal pigment epithelium of the eye exceeds the predetermined amount. A notification may be provided that one or more of the retinal treatment parameters has been automatically adjusted. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

For purposes of illustration, the present invention is directed to a process for safely providing retinal phototherapy by determining concentrations of melanin within an eye, and particularly within the retinal pigment epithelium (RPE) of the eye. Determining the concentrations of melanin within the RPE of the eye can be important in determining treatment of eye diseases. For example, if an individual has abnormally elevated concentrations or levels of melanin within the RPE this can cause unanticipated elevated heating, and thus tissue destruction, when treating the eye, and particularly the retina, with light sources, such as infrared or near infrared laser light beams, such as those used in retinal phototherapy, such as photocoagulation or photostimulation where tissue is heated as part of the therapy process. It is the level or concentrations of melanin within the RPE that is often important to determine as this is the layer which can cause excessive heating and damage when the retina is exposed to light sources during photocoagulation or photostimulation treatments.

The melanin in the eye is primarily eumelanin, and its monomer has the chemical formula $C_{18}H_{10}N_2O_4$, and a molecular weight of 318.283, with a density of 1.7 g/cc and an index of refraction of 1.772. In the RPE, melanin is contained in protein-coded organelles, called melanosomes. Inside the melanosomes, the melanin monomers, which have dimensions of less than ten Angstroms, combine to form aggregates. The aggregates have dimensions of several tens of Angstroms, and are made up of stacked sheets of covalently-bonded monomer, with the sheets having separations of 3.4 Angstroms. The sheets are held together by weaker pi-pi bonding forces.

The melanin in the RPE is derived from the neural ectoderm. In the RPE, the melanosomes are located mainly in the apical region of the RPE cells and are elongated in shape, with the long dimension aligned with the apices in order to make close contact with the rods and cones. Typical widths of all foreign RPE melanosome are 250-500 nm, and typical lengths are 640-800 nm. These give $6.5\times10^{-14}$ cubic centimeters for a typical melanosome volume. The melanin is rather densely packed in the RPE melanosomes, the melanin density in a monomer being 1.7 g/cc.

In the RPE, from the foregoing numbers, the number density of melanin is $3.38 \times 10^{18}$ cm$^{-3}$ with a mass density of $1.8 \times 10^{-3}$ g/cc, and since the melanin is all contained within melanosomes, the corresponding number density of melanosomes in the RPE is $10 \times 10^{10}$ cm$^{-3}$. This gives a linear separation between melanosomes in the RPE of 3.68 microns.

Figure 1:
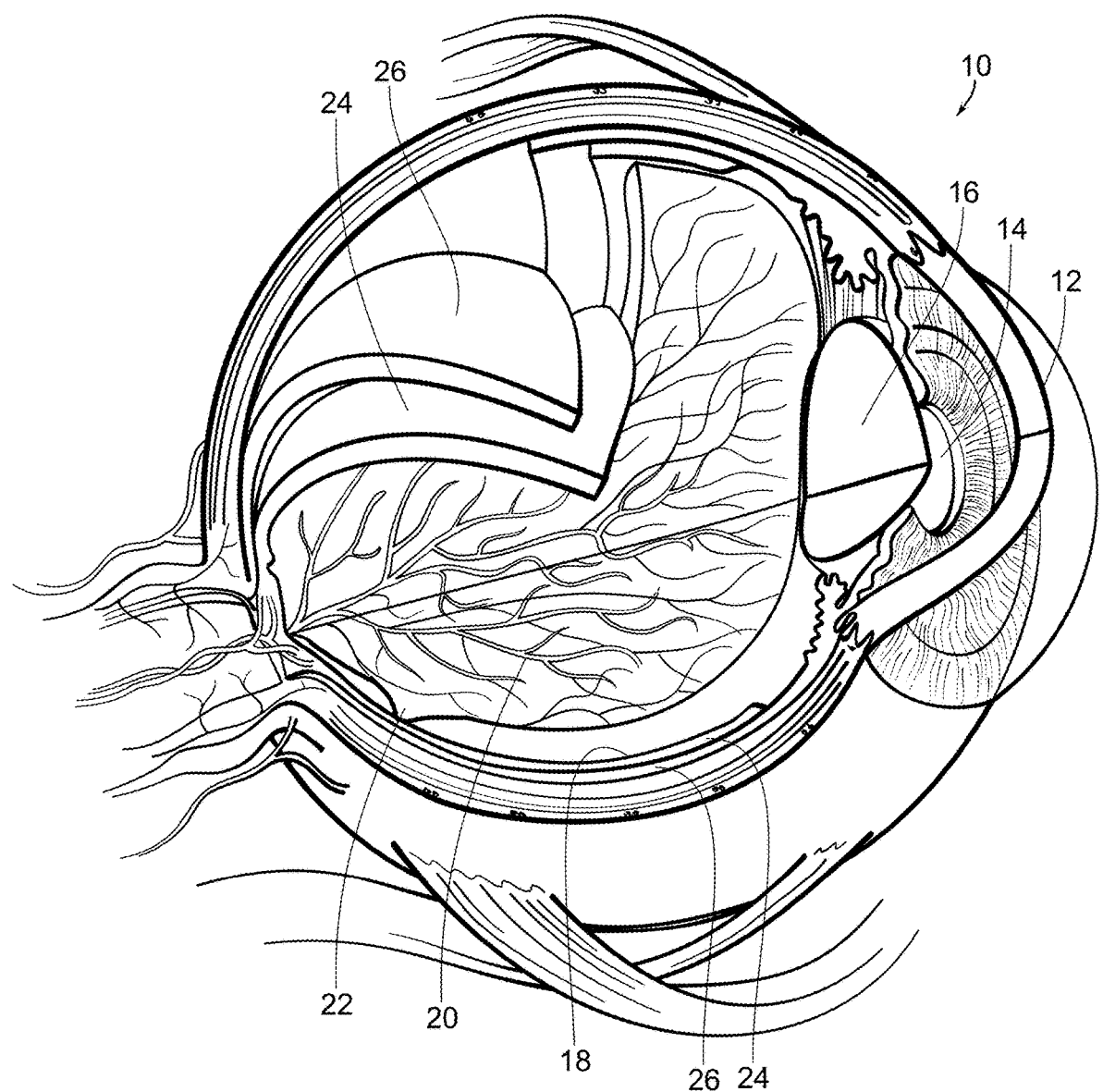
FIG. 1 is a diagrammatic view of an eye.
Figure 2:
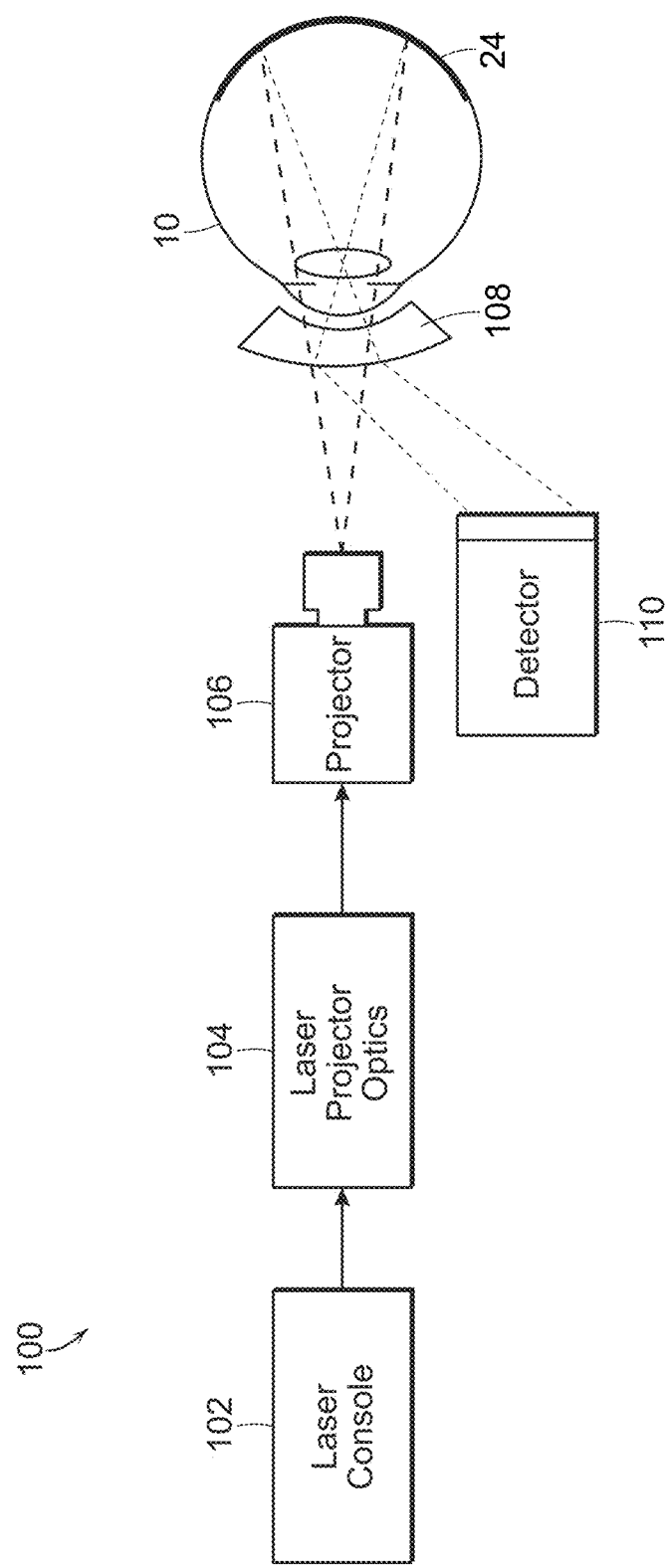
FIG. 2 is a diagrammatic view of a system used in accordance with the present invention for determining levels of melanin within an RPE of an eye.

With reference now to FIG. 2, a system 100 is shown which may be used in accordance with the present invention. Laser console 102 generates a light beam having a wavelength near infrared. The wavelength range may be between 600 nm and 1000 nm, typically between 600 nm and 850 nm. Wavelengths below the predetermined wavelength range begin to absorb and scatter light from other pigments, and wavelengths above the predetermined range of wavelengths of the present invention are increasingly absorbed by water. However, the predetermined wavelength range of the present invention, between 600 nm and 1000 nm, is ideal for measuring the melanin levels of the RPE.

The generated light beam is then passed through optics 104, which may be used to focus the light beam, filter the light beam, generate a plurality of light beams from the generated first light beam, or the like. The light beam is then passed through projector 106, which may be a retina camera or the like, for projection into the eye 10, and more particularly so as to apply the first light beam to the RPE 24 of the eye 10. Additional optics 108, as necessary, may be used to direct the light beam onto the RPE 24 of the retina. Reflections from the RPE are detected by detector 110. The detector 110 in a particularly preferred embodiment detects interferometry such as an Optical Coherent Tomography (OCT) device.

The amount of light reflected from the RPE by the light beam is measured, and then a concentration of melanin within the RPE of the eye is determined using the measured amount of light reflected from the RPE from the light beam. The determined level or concentration of melanin within the RPE can then be compared to normal anticipated or average levels of melanin within the RPE to determine if the melanin levels within the RPE of that eye are elevated or outside of the anticipated range or predetermined amount.

Figure 3:
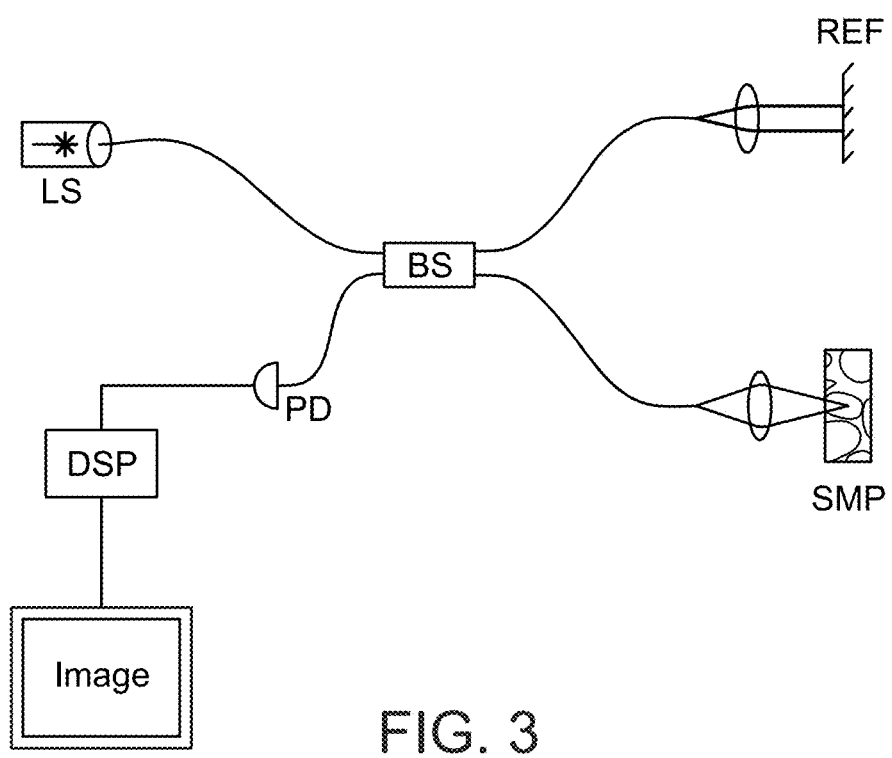
FIG. 3 is a diagrammatic view of an OCT system used in accordance with the present invention.

With reference now to FIG. 3, in a particularly preferred embodiment, an interferometric signal or pattern is generated and detected from which it can be determined if the level or concentration of melanin within the RPE is dangerously elevated. This involves generating an infrared light beam using light source (LS). As will be more fully described herein, the light beam has a wavelength of between 600 nm and 1000 nm, and more preferably a wavelength between 600 nm and 850 nm. A beam splitter (BS) splits the light beam into a reference beam (REF) and a sample beam (SMP) which is applied to the retina, and more particularly the RPE. Typically, the reference beam is applied to a movable mirror or other reference point.

With continuing reference to FIG. 3, the light beam, and more particularly the sample beam portion (SMP) of the light beam is focused to a depth resolution of the order of 3 to 10 microns which corresponds with a thickness of the RPE. Light reflected from the RPE comprises an interferometric signal or pattern which is detected, such as using a photodetector (PD). Digital signal processing (DSP) in the form of electronics, including a microcontroller and/or computer, processes the reflections and can create a displayable image (IMAGE) and/or provide the determination if the level or concentration of melanin within the RPE of the retina of the eye is elevated compared to a normal level or concentration.

Figure 4:
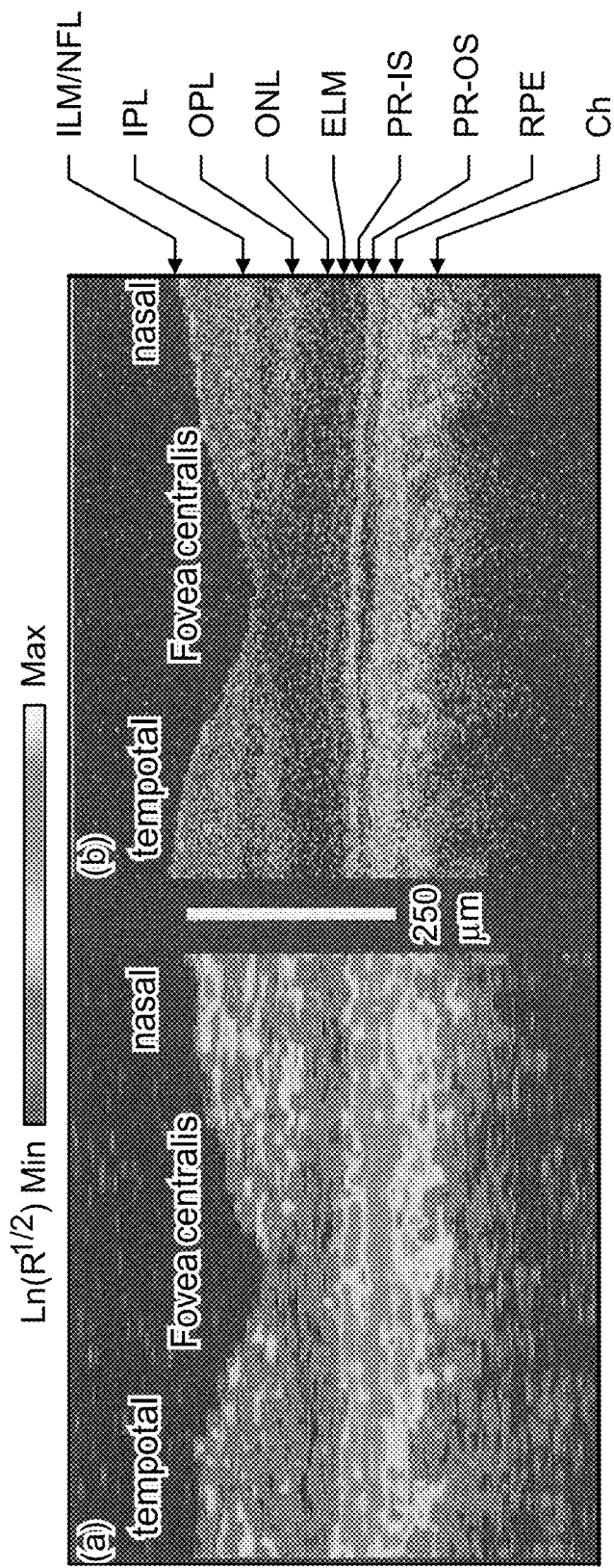
FIG. 4 are images of mappings of retinal layers of an eye using an OCT device.

Typically, the device or system which generates the near infrared light beam and detects the interferometric signal or pattern is an optical coherence tomography (OCT) device or system. The principle of OCT is light, or low coherence, interferometry. The optical setup typically consists of an interferometer with a low coherence, and a light source. Light is split into and recombined from reference in sample arm respectively, as described above. In OCT, the interference is a distance of micrometers, owing to the use of the light source used. As described above, light in an OCT system is broken into two arms, namely a sample arm containing the item of interest, and a reference arm, usually a mirror. The combination of the reflected light from the sample arm and the reference light from the reference arm gives rise to an interference pattern if the light from both arms have travelled approximately the same optical distance. By scanning the mirror in the reference arm, a reflectivity profile of the sample can be obtained, which is a time domain OCT. Areas of the sample that reflect back a lot of light will create a greater interference than areas that do not. A cross-sectional tomograph, as illustrated in FIG. 4, may be achieved by laterally combining a series of these axial depth scans. OCT can be used to obtain subsurface images of translucent or opaque materials at a resolution equivalent to a low power microscope. It will be appreciated that the OCT device generally described in FIG. 3 may have additional components, such as additional optics, cameras, filters, diffraction grading and the like as necessary. A benefit of using an OCT device in accordance with the present invention is that they are commonly used in the ophthalmological field and the data obtained therefrom can be used in accordance with the present invention or the OCT system can be modified as needed in order to accomplish the present invention.

OCT is used routinely by retinal specialists to image the retina. No matter what treatment is used, OCT is typically used to assess the general condition of the retina before treatment begins. FIG. 4 illustrates two OCT mappings of retinal layers. The OCT image on the left has a depth resolution of ten microns, and is obtained with a super luminescent diode (SLD) with a central wavelength of 843 nm. The OCT image on the right has a depth resolution of three microns, and is obtained with a TI:AL$_2$O$_3$ laser with a mean wavelength of 800 nm. The RPE in these images is typically the brightest layer.

With continuing reference to FIG. 4, an example of topographical in vivo mapping of retinal layers at the Fovea centralis along ι3 mm of the papillomacular axis is shown. The logarithm of the signal is represented on a false colour scale shown on top of the figure . . . (a) SLD: mean wavelength λ=843, Δλ=30 nm, depth resolution 10 μm. (b) Ti:Al$_2$O$_3$ laser: mean wavelength λ=800 nm, Δλnm; 3 μm depth resolution. The layers are (from top): ILM/NFL=inner limiting membrane/nerve fiber layer; IPL=inner plexiform layer; OPL=outer plexiform layer; ONL=outer nuclear level; ELM=external limiting membrane; PR-IS= photoreceptors inner segment; PR-OS=photoreceptors outer segment RPE=retinal pigment epithelium; Ch=choriocapillaris and choroid.

As mentioned above, OCT is based on low-coherence interferometry, and typically employs near infrared light. In its simplest form, in an OCT system this near-IR light is divided into two arms: a sample arm that contains the target of interest, and a reference arm that contains a movable mirror. An interference pattern arises when the reflected light from the sample arm is combined with the reflected light from the reference arm, but only if light from both arms have traveled close to the same distance. Here "close" means that the two paths must be within the "coherence length of" the radiation source. This means that for short coherence lengths, the OCT device can be "focused" on a particular depth of the target simply by adjusting the length of the reference arm by moving its mirror. By this means, all other depths of the target are excluded from contributing to the desired signal.

For an OCT, the depth resolution $\Delta z$ is often given as:

$$\Delta z = (2 \ln 2/\pi)(\lambda^2/\Delta\lambda) = 0.44(\lambda^2/\Delta\lambda) \quad [2.1]$$

This assumes an ideal Gaussian amplitude spectrum. This expression is a limiting case of the more general uncertainty relation estimate for a wave packet:

$$\Delta z\, \Delta k \approx 2\pi \quad [2.2a]$$

which, with $k=2\pi/\lambda$, $$|\Delta k| \approx 2\pi(\Delta\lambda/\lambda^2), \quad [2.2b]$$

Giving:

$$\Delta z \approx (\lambda^2/\Delta\lambda). \quad [2.3]$$

Figure 7:
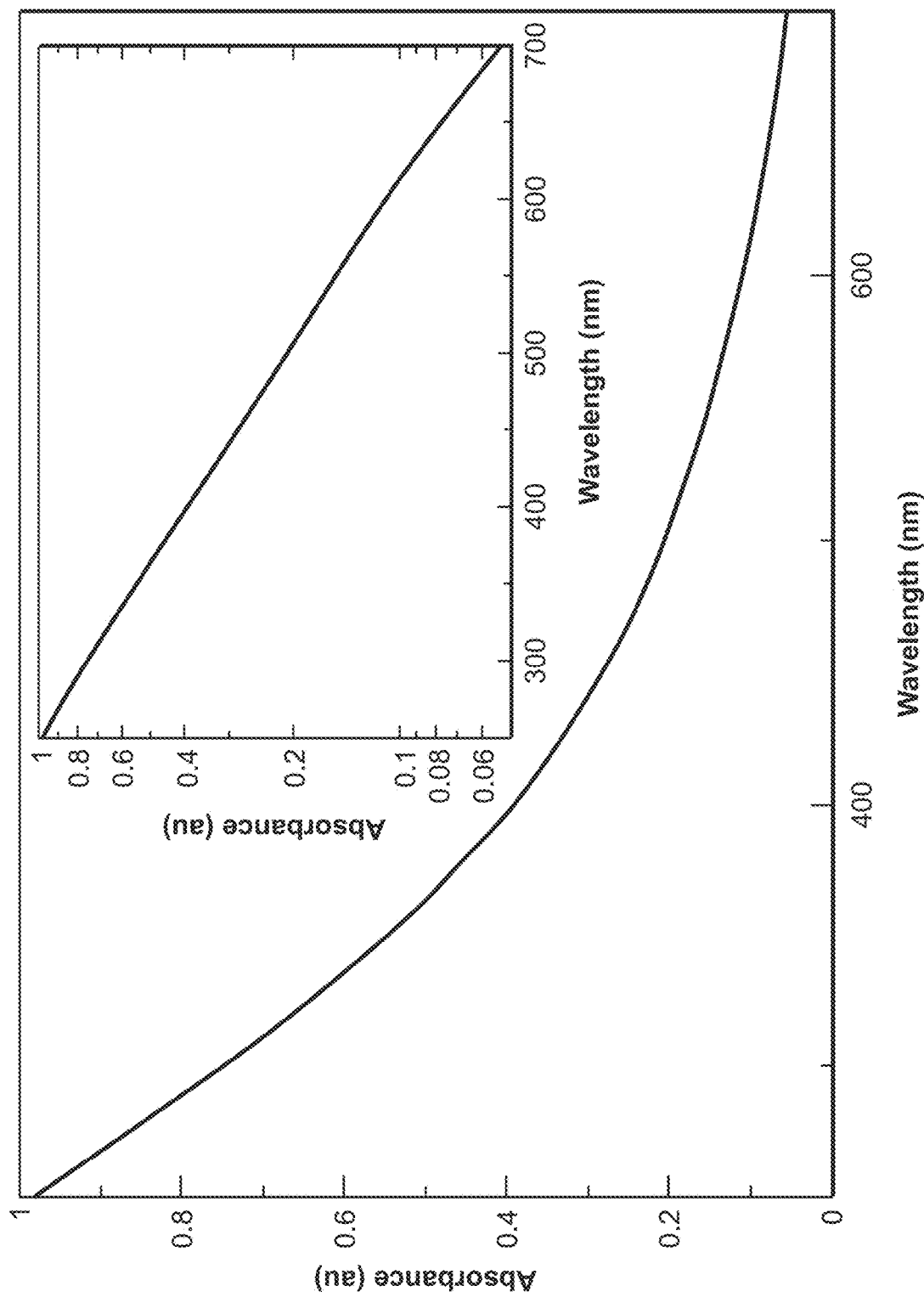
FIG. 7 is a graph illustrating absorbance of eumelanin as a function of wavelength.

For example, for the $\lambda=800$ nm and $\Delta\lambda=260$ nm case of FIG. 7, eq. [23] gives a depth resolution $\Delta z \approx 2.5$ μm, not too different from the 3 μm resolution obtained from the actual Ti:Al$_2$O$_3$ OCT system.

Treating the total electric field $E_T(t)$ at the interferometer's detector as a scalar, it can be written as the sum of the field $E_R(t+\Delta t)$ from the reference arm and the field $E_S(t)$ from the sample arm:

$$E_T(t) = E_R(t+\Delta t) + E_S(t) \quad [2.4]$$

In this expression, a time delay $\Delta t$ has been introduced in the reference signal to allow for a difference in the path lengths of the reference and sample arms.

The intensity $I(t)$ associated with each field $E(t)$ is:

$$I(t) = E^*(t)E(t). \quad [2.5]$$

We can assume that each electric field has the form:

$$E(t) = A(t)\exp[\Phi(t) - i\omega t], \quad [2.6]$$

where $A(t)\exp[\Phi(t)]$ is the envelope of the field and w is the mean angular frequency of the power spectrum of E(t). For the fields of interest in OCT, the time rates of change of the envelope are small compared to that described by the average angular frequency $\omega$.

Then the averaged intensity at the interferometer's detector is:

$$I_T(\Delta t) = \langle E_T^*(t, \Delta t) E_T(t, \Delta t) \rangle, \quad [2.7]$$

where the angular brackets indicate an ensemble average. The process can be regarded as ergodic so that the average intensity is independent of t.

On inserting eqs. [2.4]-[2.6] into eq. [2.7], there results:

$$I_T(\Delta t) = I_S + I_R + G_{SR}(\Delta t), \quad [2.8]$$

With:

$$G_{SR}(\Delta t) = 2\{I_S I_R\}^{1/2} \gamma_{SR}(\Delta t)[\alpha_{SR} - \delta_{SR}(\Delta t)]. \quad [2.9]$$

The quantity $G_{SR}(\Delta t)$ contains the desired interferometric information that gives the information about the target. In this expression, $\gamma_{SR}(\Delta t)$ is the complex degree of coherence of the two waves, $\delta_{SR}(\Delta t)$ is the phase delay with the time delay A related to the path difference $\Delta z$ between the reference and sample beams by $\Delta t = \Delta z/c$. The quantity $\alpha_{SR}$ is a constant phase of no consequence for determining information about the target.

Equation [2.9] was developed for a simple OCT in which a difference in path length is introduced between the reference and target arms by, say, a movable mirror in the reference arm. Since it arises from a correlation function between the fields from the reference and target arm, it is straightforward to apply the Wiener-Khinchine theorem relating a correlation function and a spectral power density to obtain expressions for frequency-domain OCT instruments as well. But the basic physics underlying OCT is simply low coherence interferometry between signals from a reference arm and from a sample arm.

From the description in above, OCT is based on the interference between the signals in a reference arm and a sample arm that arise from a source with a very short coherence time. Because of the very short coherence time sources used in OCT, the phenomenon is very similar to the interference between two short duration wave packets. Only when the difference between the two paths corresponds to a time difference that is shorter than the duration of the wave packet will there be an interference signal. This means that when the coherence time is very short, the peak of the interferometric signal will arise only from a given depth in the sample. This depth is determined by the movable mirror in the reference arm: the depth is just one-half of the path length of the light in the reference arm Ito and from the mirror). The signal will go to zero when the depth differs from this value by the depth resolution estimate of eq. [2.3].

The significance for measuring the melanin content of the RPE is that by choosing a source coherence distance comparable to the melanin thickness of the RPE (6-8 microns), it is possible to use OCT to isolate the contribution of the RPE melanin to the OCT signal, and thereby determine when the RPE melanin concentration is dangerously high.

Specifically, for source coherence distances of the order of 6-8 microns, the total OCT interferometric signal arising from the radiation from the RPE interacting with the reference arm signal will be determined by:

Backwards scattering from the RPE, and

Attenuation by absorption and scattering propagating through the RPE and anterior retina.

The source coherence distances in OCT are comparable to the thickness of the RPE: sometimes shorter, and sometimes longer. For example, in the two cases of FIG. 4, the coherence distances are 3 microns and 10 microns. The approximate equations developed below should suffice to give the dependences of the results on the RPE melanin content: In particular, they should be usable to estimate the relative magnitudes of the signals to be expected from normal and dangerously abnormal melanin contents.

The near IR radiation in the sample arm experiences both absorption and scattering (the latter resulting in reflection of the radiation into the interferometer's detector).

Figure 5:
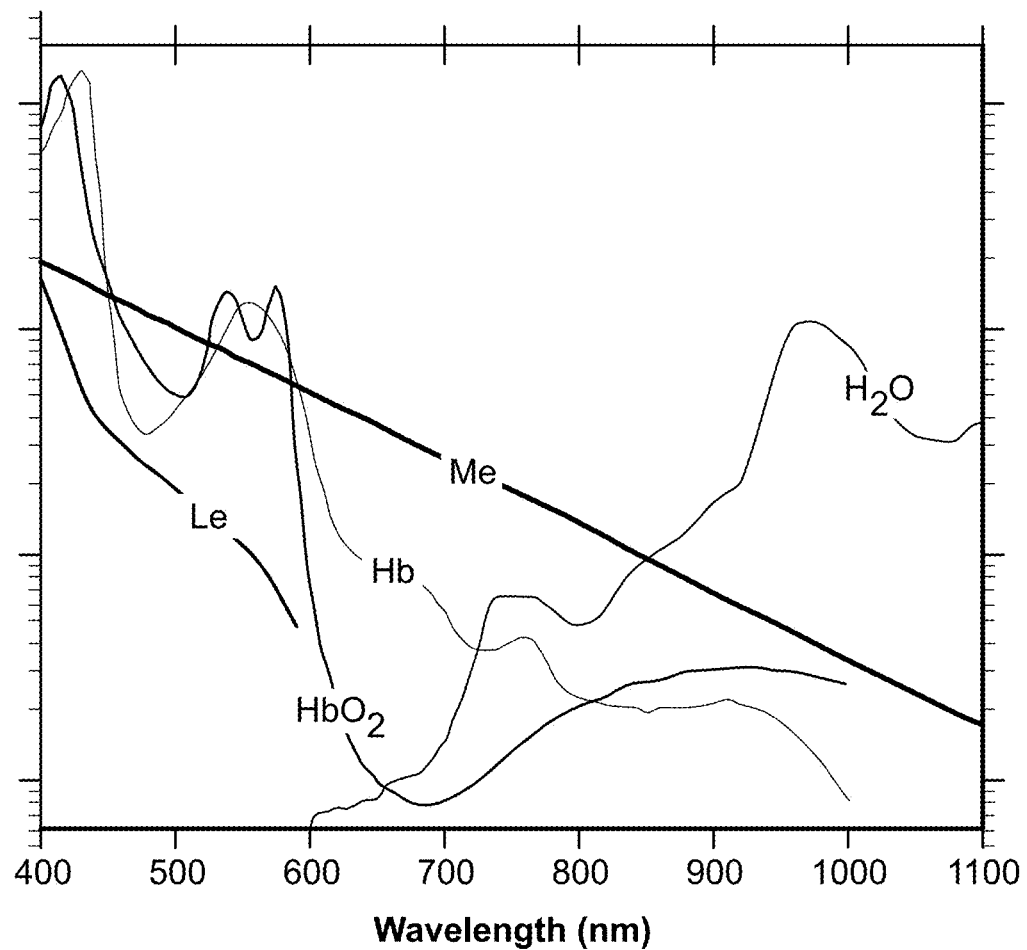
FIG. 5 is a graph illustrating wavelength dependence of the absorption of primary ocular pigments.

With reference now to FIG. 5, a graph shows the wavelength dependence primarily in the near infrared of the absorptions of the four primary ocular pigments, namely, melanin, oxygenated hemoglobin, hemoglobin and water. Also shown is the absorption of the lens. It can be seen that the absorption spectrum of melanin differs from that of all other pigments in that it is very broad. However, the RPE melanin both absorbs and scatters the radiation. In the 600-800 plus nm range, the melanin absorption is larger than the absorption of all the other pigments in the water in the eye, as shown in FIG. 5.

Figure 6:
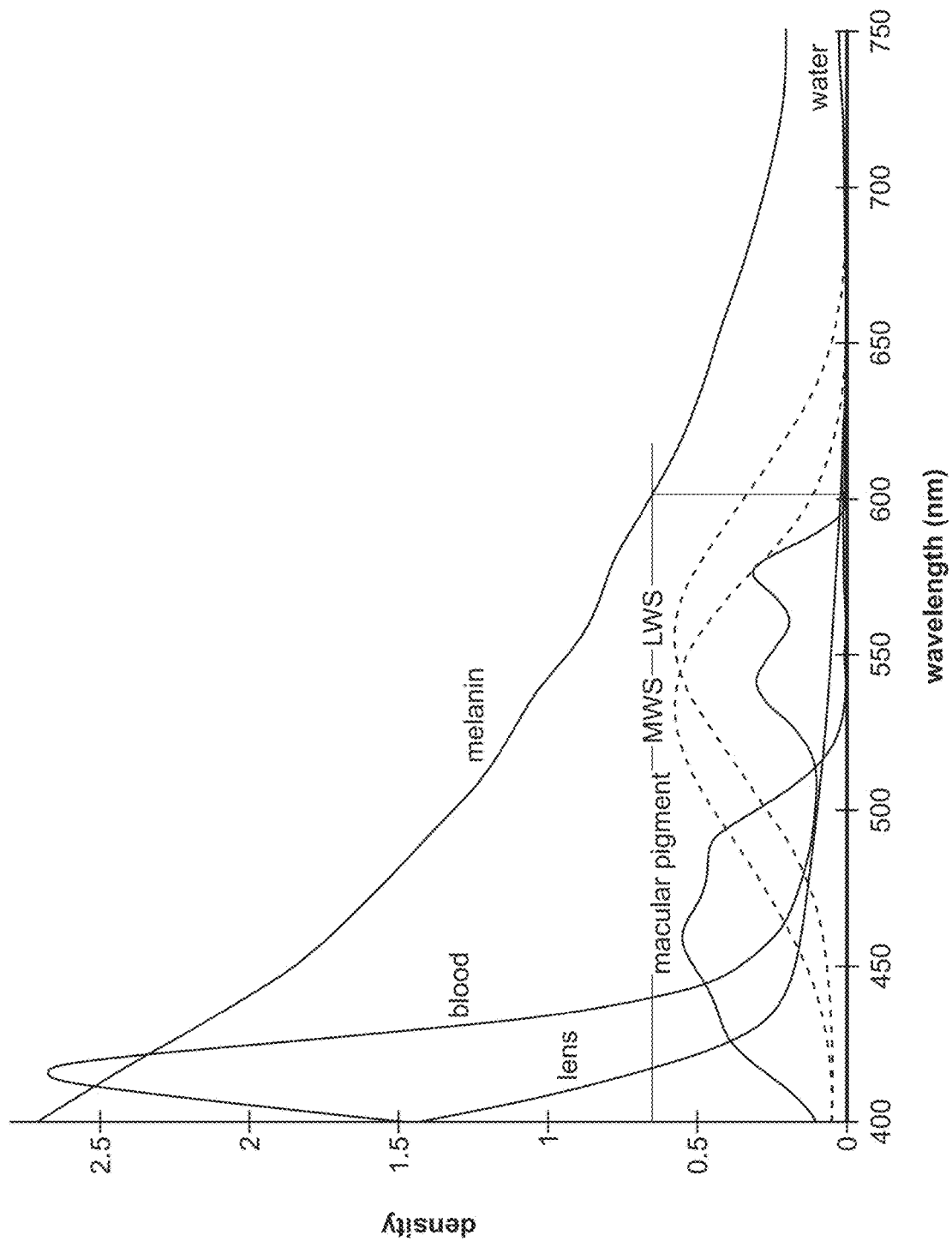
FIG. 6 is a graph illustrating wavelength dependence of absorption of primary ocular pigments in a narrower wavelength range.

With reference now to FIG. 6, the absorption of blood, melanin, macular pigments, the lens, water, long wavelength sensitive visual pigments (LWS) and medium wavelength sensitive visual pigments (MWS) primarily within the visible range of wavelengths is illustrated. The blood layer is taken to be 23 microns thick with an oxygenation of 95%. The melanin density is 1.32 at 500 nm, and the macular density is 0.54 at 460 nm. The lens density is 0.54 at 420 nm and the water density is 0.025 at 740 nm. The visual pigment densities are both 0.57 at their peaks. In the eye, melanin dominates the absorption of laser light in the wavelength range generally between 550 nm and 1000 nm, and more particularly between 600 nm and 850 nm, as shown in FIG. 6.

Prior modeling of the spectral reflectance of the human eye used values of 3.61-8.05 mmol/L for RPE melanin. The thickness of the melanin layer in the RPE is less than 10 microns, typically around 6 microns. It has been found that the melanin content in the RPE does not usually vary much from patient to patient.

As seen in FIG. 6, the absorption coefficient of melanin decreases considerably as the wavelength increases. Thus, at the lower 600 nm end of the melanin-dominated absorption window, the RPE melanin absorption is much larger than it is at the 850 nm upper end of a particularly preferred range of wavelengths. There is no general agreement as to how the melanin absorption varies with wavelength, however.

FIG. 7 is a graph illustrating the absorbance of eumelanin as a function of wavelength, particularly between 250 nm and 700 nm. Eumelanin is the dominant component of the melanin in the eye. Although there is no general agreement on the variation of the optical density with wavelength, the present invention assumes exponential dependence of $\exp[-0.062\lambda(nm)]$, which is reflected in FIG. 7. If this result is combined with the prior finding of an optical density of 0.22 at 500 nm, this gives for the two-way transmission through the RPE of:

$$\text{Transmission} = \exp[-2\alpha L] = \exp[-22.72 \exp[-0.0062\lambda(nm)]]. \quad [3.1]$$

On the other hand, if an optical density of 0.29 at 500 nm is used, then the result yields:

$$\text{Transmission} = \exp[-2\alpha L] = \exp[-29.973 \exp[-0.0062\lambda(nm)]]. \quad [3.2]$$

Figure 8:
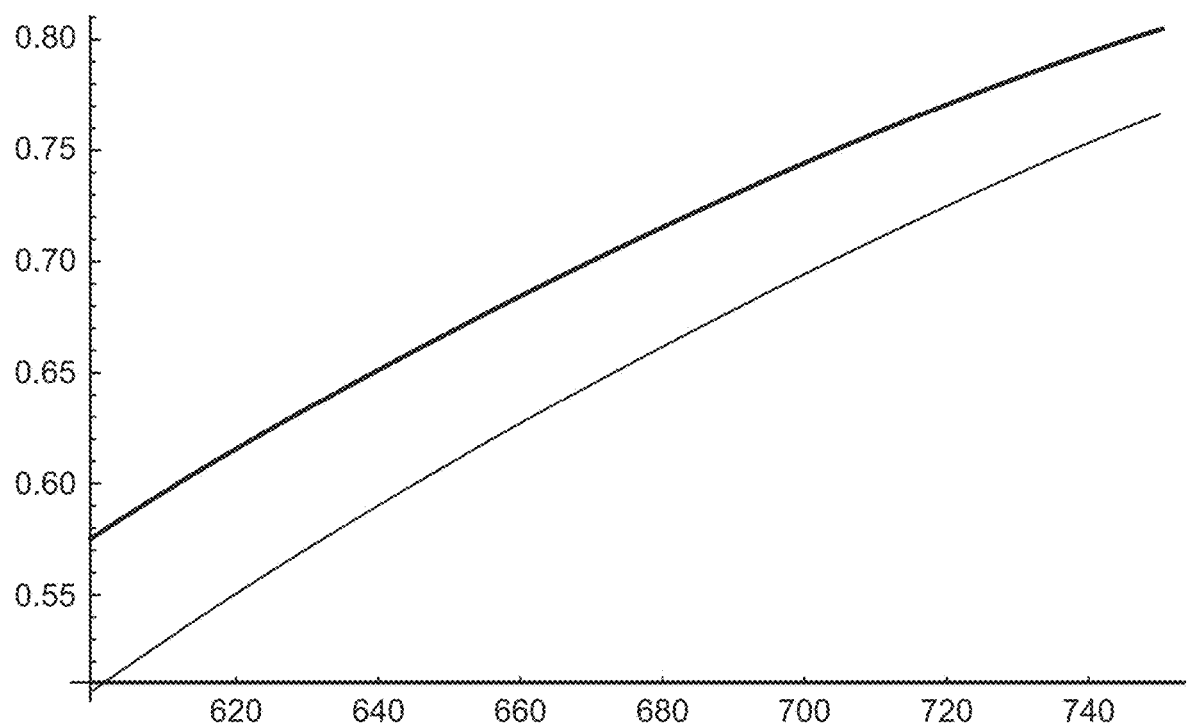
FIG. 8 is a graph depicting two-way transmission through RPE melanin at ordinary concentrations.

Equations [3.1] and [3.2] are plotted in FIG. 8, which is a graph depicting the two-way transmission (as determined by the large absorption cross-section) through the RPE melanin at ordinary concentrations. The top curve assumes that the optical density is 0.22 at 500 nm, whereas the lower curve assumes that the optical density at 500 nm is 0.29. It can be seen that towards the 850 nm limit of the melanin-dominated absorption window, the absorption coefficient of the RPE melanin is small, permitting the reflected signal from the choroid to pass through to the detector 110. At elevated, potentially dangerous, levels of RPE melanin, the reflected signal from the choroid at 600 nm is diminished considerably on passing through the RPE, while at 800 nm is not diminished nearly as much.

Figure 9:
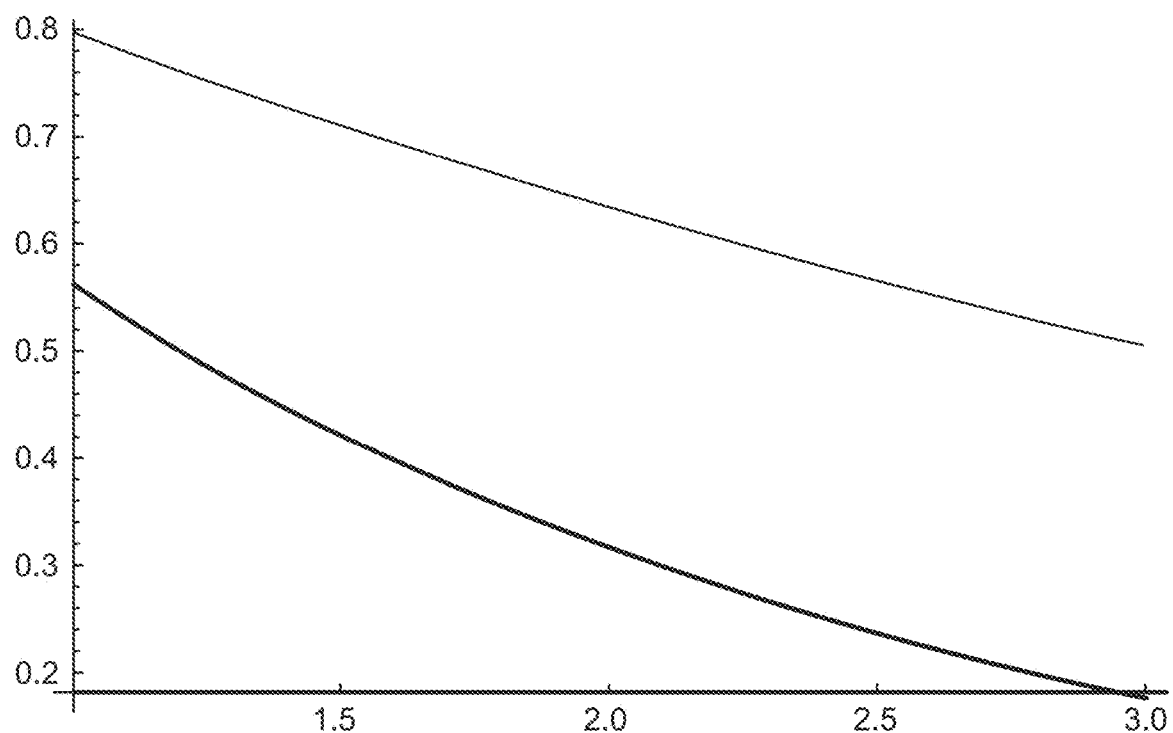
FIG. 9 is a graph illustrating variation of the RPE melanin transmission at different wavelengths.

FIG. 9 is a graph illustrating the variation of the RPE melanin transmission (as determined by the large absorption coefficient) at 750 nm (top curve) and at 600 nm (bottom curve) as the RPE melanin concentration is varied from normal (n=1) to an elevated, danger threshold of three times normal (n=3). In FIG. 9, it is assumed that the optical density of 500 nm is 0.22 for a normal RPE concentration. With continuing reference to FIG. 9, the graph shows the behavior of the RPE melanin transmission at 600 nm and 750 nm as the concentration is varied from normal (n=1) to a dangerous level of three times normal (n=3). The graph of FIG. 9 shows that at 600 nm the transmitted signal is diminished by a factor of close to 4, while at 750 nm it is only diminished by a factor of approximately 1.5. This large difference, however, may be mitigated somewhat by other factors in the expression for reflectivity.

In addition to being the dominant absorber of radiation in the 600 nm-800 nm plus range of wavelengths, melanin also scatters the radiation. Melanin is densely packed in the melanosomes. As described above, in the RPE the melanosomes are elongated in shape and make close contact with the rods and cones. The melanosomes are regarded as the basic scattering entities. The melanosomes have dimensions comparable to the 600 nm-850 nm wavelengths of interest. A typical RPE melanosome has dimensions of 250-400 nm (average 300 nm) wide by 640 nm-800 nm (average 720 nm) long.

Accordingly, the scattering in this range of wavelengths is in the Mie scattering domain. For Mie scattering, the asymptotic scattering cross section in the backwards direction is roughly proportional to $\lambda^2$. The resulting cross section for backwards scattering from a melanosome in the RPE is:

$$\sigma_{sRPE} \approx 0.05 \times 10^{-14} \lambda nm^2 \, cm^2, \quad [3.3]$$

where $\lambda_{nm}$ denotes the wavelength expressed in nanometers.

Although the absorption is dominated by the melanin in the 600 nm-800+nm range of wavelengths, scattering can also result from the structural matrix in which the melanosomes are imbedded. It has been determined that the scattering properties of the retina and the choroid from OCT scans for a wavelength of 855 nm in the retina is:

Scattering coefficient $1.64 \times 10^{-4} \lambda nm2_{RPE} = 120 \, cm^{-1}$
Anisotropic factor $g_{RPE} = \langle \cos \theta \rangle = 0.97$ The backwards scattering coefficient is obtained from the scattering coefficient by multiplying it by $(1-g)$.

The scattering occurs due to mismatches in refractive index of the different tissue components, ranging from cell membranes to whole cells. Cell nuclei and mitochondria are the most important scatterers. Their dimensions range from 100 nm to 6 µm, and thus fall within the NIR window. Most of these organelles fall in the Mie region, and exhibit highly anisotropic forward-directed scattering.

The above only gives the scattering coefficient and anisotropic factor for the entire retina and not for the RPE layer that forms the back layer of the retina, individually. We shall approximate the RPE scattering coefficient and anisotropic factor by using the total retinal quantities.

We shall apply the $\lambda^2$ factor of eq. [3.3] to determine the scattering coefficients at other wavelengths, resulting in:

$$\mu_{backscatRPE} = (1-0.97)120(\lambda_{nm}/855)^2 = 4.92 \times 10^{-6} \lambda_{nm}^2 \, cm^{-1} \quad [3.4]$$

These can be compared with the scattering coefficients from melanin for normal melanosome densities ($N_{RPE} = 2 \times 10^{10} \, cm^{-3}$)

$$\mu_{sRPE} = 2 \times 10^{10} \times 0.05 \times 10^{-14} \lambda_{nm}^2 = 1 \times 10^{-5} \lambda_{nm}^2 \, cm^{-1}$$
[normal RPE melanin density] [3.5]

We see that scattering from the structural matrix in the RPE is less than that from the melanin. The scattering coefficients are also smaller than what the above gives for the coefficient of absorption at normal melanin densities:

$$\mu_{aRPE} = 2 \times 10^{10} \times 9.47 \times 10^{-7} \exp[-0.0062\lambda_{nm}] = 1.89 \times 10^4 \exp[-0.0062\lambda_{nm}] \quad [3.6]$$

The melanosome number densities and scattering cross sections indicate that not much scattering occurs in traversing either the RPE for radiation with wavelengths in the 600-800+ nm range of wavelengths. This is much less than the optical density for absorption by the melanin. The scattering optical density in the anterior retina is also small.

In the RPE with a melanosome density of $2 \times 10^{10}$ cm$^{-3}$, the mean free path is:

$$\Lambda_{mfp} = 1/9.54 = 0.0.1 \text{ cm, i.e. 1000 microns.} \quad [3.7]$$

This is much larger than the 6-10 micron thickness of the RPE, so the probability that a photon is scattered on traversing the RPE is very small indeed. The optical density for scattering in the RPE is:

$$OD_{scattering\ in\ RPE} = \mu_{scat} w = 9.54 \times 0.0006/2.303 = 0.004. \quad [3.8]$$

This is much less than the optical density for absorption by the melanin. The scattering optical density in the anterior retina is also small. Accordingly, in the 600-800 nm range of wavelengths, absorption is more important than scattering in the RPE.

Because the scattering of the near IR radiation in the RPE is so small, we shall use the transport equations developed by Kubelka and Munk (1931). More exact treatments are possible using Monte Carlo numerical methods [See, e.g., Preece and Claridge (2002)], but we use the simple Kubelka-Munk equations here in order to develop a simple intuition for the dependence of the OCT results on the relevant parameters.

The treatment is similar to that for calculating the total reflectivity. However, it differs from the latter since the interference signal for a low coherence source with a time delay corresponding to a point within the RPE and a depth resolution comparable to the thickness of the RPE, means that no contribution to the signal will arise from the choroid.

Moreover, we have seen that the cross section for absorption is large only for the RPE, and so we shall ignore attenuation of the radiation through the anterior portion of the retina. (This should be sufficient for showing how the relative signals received by the interferometer's detector from a normal melanin concentration in the RPE and a dangerously high level of RPE melanin concentration.).

Accordingly, we shall assume that the short coherence interferometric signal arises only from radiation reflected (and attenuated) in the RPE itself. The approximate transport equations in the steady state are:

$$dI(+)/dx = -[N(\sigma_s + \sigma_a) + \mu_{back\ scat}] I(+) + [N\sigma_s + \mu_{back\ scat}] I(-) \quad [3.9]$$

$$dI(-)/dy = -[N(\sigma_s + \sigma_a) + \mu_{back\ scat}] I(-) + [N\sigma_s + \mu_{back\ scat}] I(-) \quad [3.10]$$

Here,

I(+) is the intensity of the input radiation as it travels through the RPE;

I(−) is the intensity of the reflected radiation as it travels backwards through the RPE to the front of the RPE;

x is the distance into the RPE measured from the front of the RPE;

y=w−x, where w is the thickness of the RPE melanin layer;

N is the number density of the melanin aggregates that absorb and scatter the radiation;

$\sigma_s$ denotes the cross section of a melanin aggregate for backwards scattering;

$\sigma_a$ denotes the cross section of a melanin aggregate for absorption; and $\mu_{back\ scat}$ is the coefficient for backscattering from the structural matrix.

It has been demonstrated experimentally that $\sigma_a/(\sigma_s + \sigma_a)$ is quite large, scattering contributing less than 6% to the total optical attenuation across all wavelengths in the UV and optical range. The quantity $N(\sigma_s + \sigma_a) w$ is simply 2.303× the total attenuation (absorption pus scattering) optical density of the RPE melanin layer. Equations [3.9] and [3.10] can be further simplified by ignoring the term $+N\sigma_s I(-)$ in eq. [3.9], the rationale for this being that the reflected signal I(−) is much smaller than the input signal I(+). Then, on requiring that:

$$I(+) \text{ at } x=0 \text{ equals the input intensity } I_o \quad [3.11]$$

$$I(-) \text{ at } x=w \text{ equals 0 at } x=w \quad [3.12]$$

The equations can be solved directly to give for the output intensity I(−) at x=0

$$I(-, x=0) = I(+,x=0)[\{N\sigma_s + \mu_{backscat}\}_{RPE}/\{2N(\sigma_s + \sigma_a) + 2\mu_{backscat}\}_{RPE}] \text{times}$$

$$[1 - \exp[-2w\{N(\sigma_s + \sigma_a) + \mu_{backscat}\}_{RPE}]] \quad [3.11]$$

The subscript "RPE" has been added in eq. [3.11] to indicate that the quantities are for the RPE.

From eq. [2.9], the OCT interferometric signal is proportional to $\{I(-, x=0)I(+,x=0)\}^{1/2}$ $$\text{OCT signal} = \text{constant} \times I(+,x=0)[\{N\sigma_s + \mu_{backscat}\}_{RPE}/\{2N(\sigma_s + \sigma_a) + 2\mu_{backscat}\}_{RPE}]^{1/2} \times$$

$$[1 - \exp[-2w\{N(\sigma_s + \sigma_a) + \mu_{backscat}\}_{RPE}]]^{1/2} \quad [3.12]$$

where the constant is determined by the specifics of the system's efficiencies and geometry.

To avoid questions of system specifics, we shall focus our attention on the ratio of the OCT signals for abnormal and normal RPE densities:

OCT signal (abnormal RPE melanin density)/OCT signal (normal RPE melanin density=

$$[\{N\sigma_s + \mu_{backscat}\}_{RPE}/\{2N(\sigma_s + \sigma_a) + 2\mu_{backscat}\}_{REP}] \text{ times}$$

$$[1 - \exp[-2w\{N(\sigma_s + \sigma_a) + \mu_{backscat}\}_{RPE}]] \quad [3.13]$$

Figure 10:
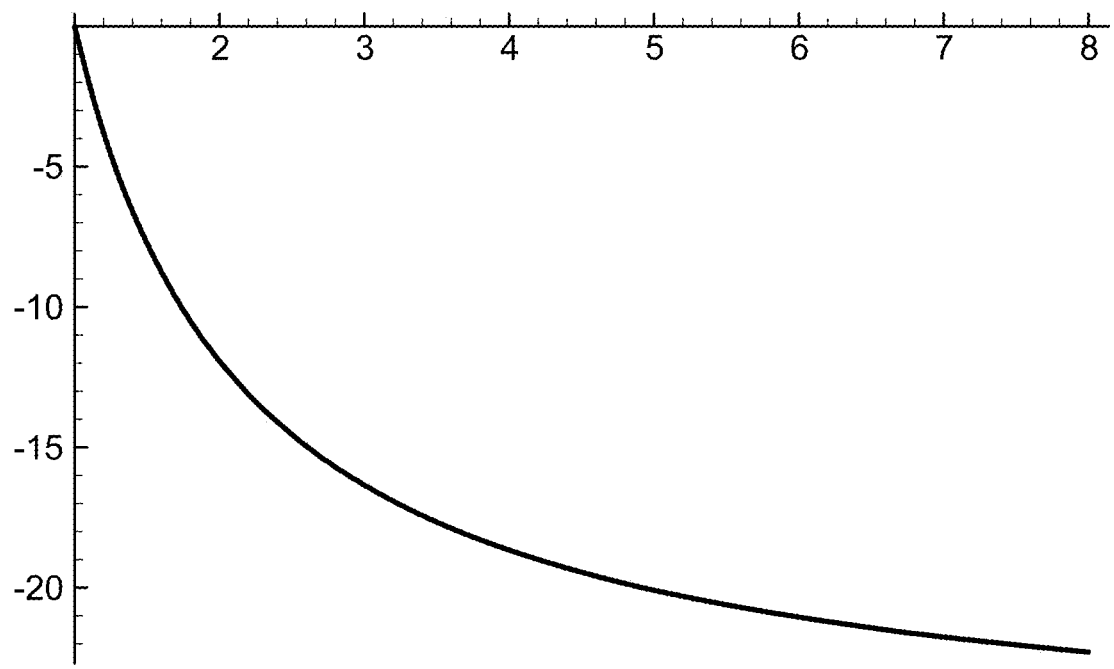
FIG. 10 is a graph depicting the percentage change in OCT signal representing the ratio of RPE melanosome density to normal density.

With reference now to FIG. 10, a plot illustrating the percentage change in the OCT signal given by eqs. [3.12] and [3.13] as the RPE melanosome density increases from its normal value of $2 \times 10^{10}$ cm$^{-3}$ by a factor of n. FIG. 10 illustrates the percentage change in the OCT signal of equation [3.12] versus n, wherein n is the ratio of abnormal RPE melanosome density to which normal density of $2 \times 10^{10}$ cm$^{-3}$. FIG. 10 shows that a 20% change in the OCT signal results from an increase in the RPE melanosome density by a factor of about five. Danger thresholds of 3-8 times normal RPE melanosome densities result in a decrease in the OCT signal of the order of 10%, and can be reliably measured by photoelectric cells or other similar detectors. Pre-treatment low coherence optical coherent tomography (OCT) with a central wavelength in the 600-900 nm wavelength range and a depth resolution of the order of 3-10 microns can be used to detect dangerous levels of RPE melanin concentrations. Photocells are quite capable of detecting the type of changes indicated in FIG. 10. This suggests that a photodetector could be used to obtain reliable detection of the danger threshold percentage changes in the brightness. This can be done by either accessing the photoelectric signal of the OCT detector directly or by using a photocell to measure the brightness of the OCT visual display. This can be compared to what would be considered a normal melanin RPE level content, which is on the order of $2 \times 10^{10}$ cm$^{-3}$ for a normal patient.

It should be noted that the RPE melanin concentration varies with lateral position in the eye. It peaks at the center of the macula and then decreases on either side over a range of approximately 5° to a relatively constant value for about 10° on either side, before rising again towards the equator at −20° and +15°. To get consistent results, it is best to operate the detector 110 in the regions where the concentration is relatively constant, or in other words on the order of approximately 10° away from the center of the macula.

Table 1 below shows the peak laser power for a phototherapy retinal treatment that will maintain the Arrhenius integral for HSP activation at a conservative value of unity when the RPE melanin content takes on different values. Peak power for different values of spot radius, train duration, duty cycle and abnormal RPE melanin ratio content is shown. The table assumes a treatment pulsed wavelength at 810 nm.

TABLE 1

| R (micron) | tF (sec) | dc (%) | α/αnormal | Psdm (watts) |
|---|---|---|---|---|
| 100 | 0.2 | 2 | 1 | 3.44 |
|  |  |  | 3 | 3.14 |
|  |  |  | 5 | 0.69 |
|  |  |  | 8 | 0.43 |
| 100 | 0.2 | 3 | 1 | 2.29 |
|  |  |  | 3 | 0.76 |
|  |  |  | 5 | 0.46 |
|  |  |  | 8 | 0.29 |
| 100 | 0.2 | 4 | 1 | 1.72 |
|  |  |  | 3 | 0.57 |
|  |  |  | 5 | 0.34 |
|  |  |  | 8 | 0.21 |
| 100 | 0.2 | 5 | 1 | 1.38 |
|  |  |  | 3 | 0.46 |
|  |  |  | 5 | 0.28 |
|  |  |  | 8 | 0.17 |
| 100 | 0.3 | 2 | 1 | 2.68 |
|  |  |  | 3 | 0.89 |
|  |  |  | 5 | 0.54 |
|  |  |  | 8 | 0.33 |
| 100 | 0.3 | 3 | 1 | 1.79 |
|  |  |  | 3 | 0.6 |
|  |  |  | 5 | 0.36 |
|  |  |  | 8 | 0.22 |
| 100 | 0.3 | 4 | 1 | 1.34 |
|  |  |  | 3 | 0.45 |
|  |  |  | 5 | 0.27 |
|  |  |  | 8 | 0.17 |
| 100 | 0.3 | 5 | 1 | 1.07 |
|  |  |  | 3 | 0.36 |
|  |  |  | 5 | 0.21 |
|  |  |  | 8 | 0.14 |
| 100 | 0.4 | 2 | 1 | 2.14 |
|  |  |  | 3 | 0.71 |
|  |  |  | 5 | 0.43 |
|  |  |  | 8 | 0.27 |
| 100 | 0.4 | 3 | 1 | 1.43 |
|  |  |  | 3 | 0.48 |
|  |  |  | 5 | 0.29 |
|  |  |  | 8 | 0.18 |
| 100 | 0.4 | 4 | 1 | 1.07 |
|  |  |  | 3 | 0.36 |
|  |  |  | 5 | 0.21 |
|  |  |  | 8 | 0.13 |
| 100 | 0.4 | 5 | 1 | 0.86 |
|  |  |  | 3 | 0.29 |
|  |  |  | 5 | 0.17 |
|  |  |  | 8 | 0.11 |
| 100 | 0.5 | 2 | 1 | 1.72 |
|  |  |  | 3 | 0.57 |
|  |  |  | 5 | 0.34 |
|  |  |  | 8 | 0.21 |
| 100 | 0.5 | 3 | 1 | 1.15 |
|  |  |  | 3 | 0.38 |
|  |  |  | 5 | 0.23 |
|  |  |  | 8 | 0.14 |
| 100 | 0.5 | 4 | 1 | 0.86 |
|  |  |  | 3 | 0.29 |
|  |  |  | 5 | 0.17 |
|  |  |  | 8 | 0.11 |
| 100 | 0.5 | 5 | 1 | 0.69 |
|  |  |  | 3 | 0.23 |
|  |  |  | 5 | 0.14 |
|  |  |  | 8 | 0.09 |
| 200 | 0.2 | 2 | 1 | 6.88 |
|  |  |  | 3 | 2.29 |
|  |  |  | 5 | 1.38 |
|  |  |  | 8 | 0.86 |
| 200 | 0.2 | 3 | 1 | 4.59 |
|  |  |  | 3 | 1.53 |
|  |  |  | 5 | 0.92 |
|  |  |  | 8 | 0.57 |
| 200 | 0.2 | 4 | 1 | 3.44 |
|  |  |  | 3 | 1.15 |
|  |  |  | 5 | 0.69 |
|  |  |  | 8 | 0.43 |
| 200 | 0.2 | 5 | 1 | 2.75 |
|  |  |  | 3 | 0.92 |
|  |  |  | 5 | 0.55 |
|  |  |  | 8 | 0.34 |
| 200 | 0.3 | 2 | 1 | 5.36 |
|  |  |  | 3 | 1.79 |
|  |  |  | 5 | 1.07 |
|  |  |  | 8 | 0.67 |
| 200 | 0.3 | 3 | 1 | 3.57 |
|  |  |  | 3 | 1.19 |
|  |  |  | 5 | 0.71 |
|  |  |  | 8 | 0.45 |
| 200 | 0.3 | 4 | 1 | 2.68 |
|  |  |  | 3 | 0.89 |
|  |  |  | 5 | 0.54 |
|  |  |  | 8 | 0.33 |
| 200 | 0.3 | 5 | 1 | 2.14 |
|  |  |  | 3 | 0.71 |
|  |  |  | 5 | 0.43 |
|  |  |  | 8 | 0.27 |
| 200 | 0.4 | 2 | 1 | 4.28 |
|  |  |  | 3 | 1.43 |
|  |  |  | 5 | 0.86 |
|  |  |  | 8 | 0.54 |
| 200 | 0.4 | 3 | 1 | 2.85 |
|  |  |  | 3 | 0.95 |
|  |  |  | 5 | 0.57 |
|  |  |  | 8 | 0.36 |
| 200 | 0.4 | 4 | 1 | 2.14 |
|  |  |  | 2 | 0.71 |
|  |  |  | 5 | 0.43 |
|  |  |  | 8 | 0.27 |
| 200 | 0.4 | 5 | 1 | 1.71 |
|  |  |  | 3 | 0.57 |
|  |  |  | 5 | 0.34 |
|  |  |  | 8 | 0.21 |
| 200 | 0.5 | 2 | 1 | 3.44 |
|  |  |  | 3 | 1.15 |
|  |  |  | 5 | 0.69 |
|  |  |  | 8 | 0.43 |
| 200 | 0.5 | 3 | 1 | 2.3 |
|  |  |  | 3 | 0.77 |
|  |  |  | 5 | 0.28 |
|  |  |  | 8 | 0.29 |
| 200 | 0.5 | 4 | 1 | 1.72 |
|  |  |  | 3 | 0.57 |
|  |  |  | 5 | 0.34 |
|  |  |  | 8 | 0.22 |
| 200 | 0.5 | 5 | 1 | 1.38 |
|  |  |  | 3 | 0.46 |
|  |  |  | 5 | 0.28 |
|  |  |  | 8 | 0.17 |

As shown in Table 1 above, the range of the ratio of abnormal RPE melanin content to normal RPE melanin content has been taken to a range between one and eight. The peak laser power depends on the laser spot radius at the retina, the duration of the micropulse train and the duty cycle. For each of these cases, the ratio of abnormal to normal RPE melanin content has been taken to be 1, 3, 5 and 8.

Any abnormal RPE melanin content manifests itself through a change in the absorption coefficient of the RPE to the incoming laser radiation: the absorption coefficient is proportional to the total RPE melanin content. Accordingly, in the table, RPE melanin content is represented by four values of the ratio of the absorption coefficient a to the normal absorption coefficient $\alpha_{normal}$:

$\alpha/\alpha_{normal}$=1, 3, 5, 8.

The effect of melanin content on the peak laser treatment power $P_{sdm}$ depends on the laser's retinal spot radius (R), the duration of the micropulse train ($t_F$), and the duty cycle (dc) of the micropulse train ($t_F$). In the table, examples are given for $P_{sdm}$ (in watts) for all possible combinations of:

R=100 microns, 200 microns
$t_F$=0.2 sec, 0.3 sec, 0.4 sec, and 0.5 sec
dc=2%, 3%, 4%, 5%
for each of the four values of the ratio $\alpha/\alpha_{normal}$.

The value of $\lambda_{nm}$ shown is the value of the peak power that maintains the Arrhenius integral for heat shock protein (HSP) activation $\Omega_{hsp}$ at a (conservative) treatment value of unity:

$\Omega_{hsp}$=1.

And it has been assumed that the treatment laser wavelength is 810 nm—for which $\alpha_{normal}$=104 cm$^{-1}$.

For an arbitrary near-IR wavelength (in nanometers) $\lambda_{nm}$, the treatment powers in the table should be multiplied by the factor $\xi(\lambda_{nm})$:

$\xi(\lambda_{nm})$=Exp[0.0062(810−$\lambda_{nm}$)], i.e.

$P_{sdm}(\lambda_{nm})=P_{sdm}\xi(\lambda_{nm})=P_{sdm}$(table value)×Exp[0.0062(810−$\lambda_{nm}$)].

From the foregoing, it can be seen that $P_{sdm}$ decreases as $\alpha/\alpha_{normal}$ increases; the values of $P_{sdm}$ are larger the larger the spot radius (R) is; the values of $P_{sdm}$ are larger the smaller the train duration $t_F$ is; and the values of $P_{sdm}$ are larger the smaller the duty cycle (dc) is.

Figure 11:
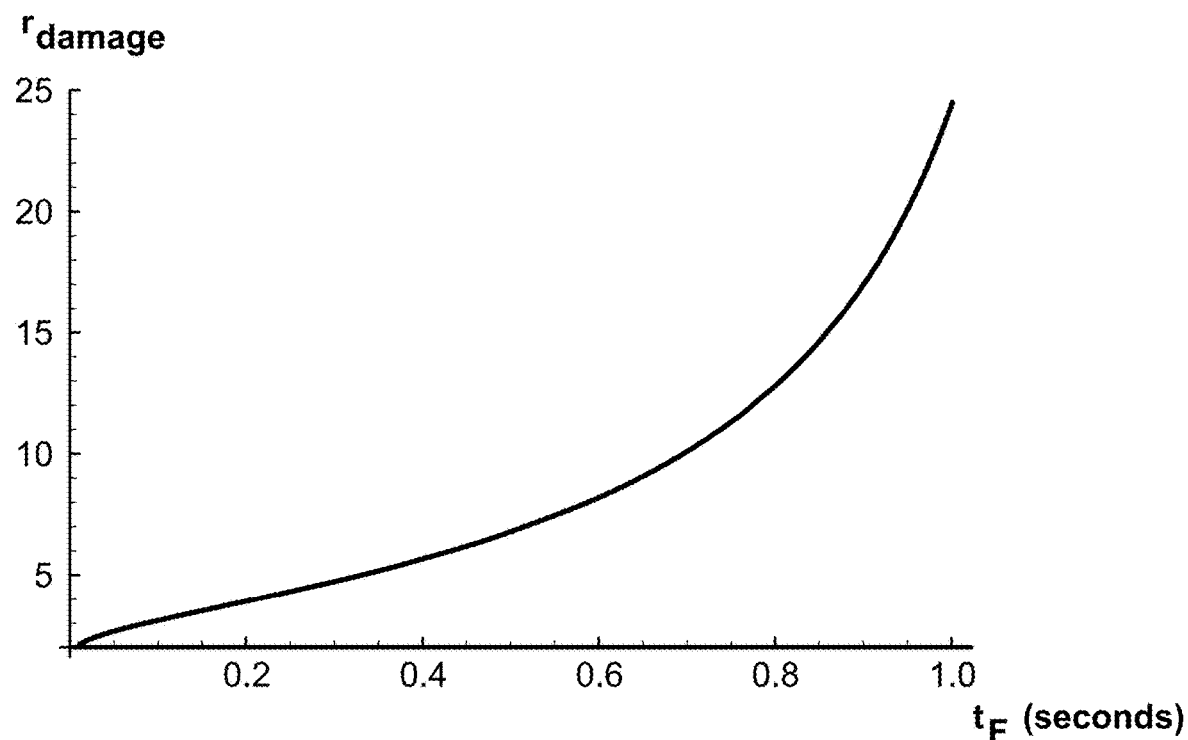
FIG. 11 is a graph showing the damage ratio of abnormal RPE melanin content to normal RPE melanin content at which damage can occur compared to a pulse train duration of pulsed light phototherapy.
Figure 12:
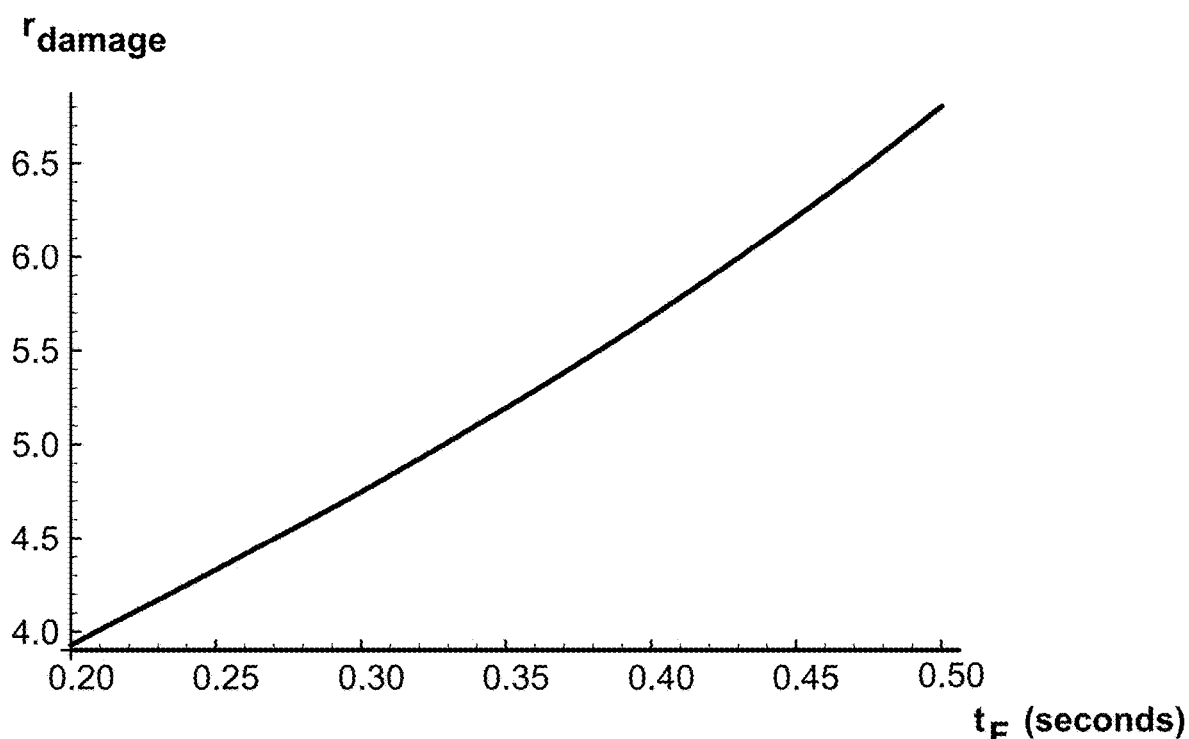
FIG. 12 is a graph similar to FIG. 11, illustrating the damage ratio in a range of 200 milliseconds to 500 milliseconds of light phototherapy pulse train duration.

FIGS. 11 and 12 are graphs that show the ratio $r_{damage}$ of abnormal RPE melanin content to normal RPE melanin content at which damage can occur. These graphs are based on rough approximate expressions for the Arrhenius integrals for HSP activation and for damage that give surprisingly close matches to the exact expressions. Both graphs plot the ratio $r_{damage}$ vs the pulse train duration $t_F$. The graph of FIG. 11 covers the range of $t_F$ from 0.01 sec to 1 sec. The graph of FIG. 12 covers a more realistic clinical range of $t_F$ from 0.2 to 0.5 sec.

As can be seen in FIGS. 11 and 12, the critical ratio $r_{damage}$ of abnormal RPE melanin content to normal RPE melanin content at which damage can occur varies from 3 to about 8 for pulse train durations ranging from 0.2 sec to 0.5 sec. Thus, one or more treatment parameters, as described above, are adjusted when the content of melanin in the RPE is determined to be at least three times greater than a normal content of melanin in the RPE. Thus, assuming a normal RPE density of 2×10$^{10}$ cm$^{-3}$, the one or more treatment parameters are adjusted when the content of melanin in the RPE is determined to be greater than 6×10$^{10}$ cm$^{-3}$.

At this critical ratio, damage can be avoided and effective HSP activation can be assured, by changing the treatment parameters from their normal values. For example, for most clinical treatment parameters of interest:

The peak power P can be reduced from its normal value $P_{normal}$ to lie in the range;

$P_{normal}/r_{damage}$<P<$P_{normal}$, if the duty cycle and retinal spot radius are left at their normal values.

The duty cycle dc can be reduced from its normal value $dc_{normal}$ to lie in the range:

$dc_{normal}/r_{damage}$<dc<$dc_{normal}$, if the laser peak power and retinal spot radius are left at their normal values.

The retinal spot radius R can be increased from its normal value $R_{normal}$ to lie in the range:

$R_{normal}$<R<$R_{normal} r_{damage}$, if the laser peak power and duty cycle are left at their normal values.

Although a single laser phototherapy parameter may be adjusted, it will be understood that more than one of these parameters can also be adjusted simultaneously. For example, the laser spot radius can be increased in diameter and the power lessened, but not lessened to the extent it would otherwise require if only the power were lessened. Similarly, all of the parameters can be adjusted slightly, such as slightly increasing the retinal spot size for the treatment light beam, lowering the pulse train duration of the treatment light beam, lowering the duty cycle of the treatment light beam, and lowering the power of the treatment light beam such that unity in the Arrhenius integral is achieved in order to avoid damage to the retina and eye of the patient having an abnormally large concentration or amount of melanin in his or her RPE.

Although several embodiments have been described in detail for purposes of illustration, various modifications may be made without departing from the scope and spirit of the invention. Accordingly, the invention is not to be limited, except as by the appended claims.

What is claimed is:

1. A process for safely providing retinal phototherapy, comprising the steps of:
    generating an interferometric signal or pattern including applying a near infrared light beam to a retina of an eye;
    detecting the interferometric signal or pattern;
    determining if a level or concentration of melanin within the retinal pigment epithelium of the retina of the eye is elevated compared to a normal level or concentration using the detected interferometric signal or pattern; and
    adjusting one or more treatment parameters of the retinal phototherapy if the level or concentration of melanin in the retinal pigment epithelium of the eye exceeds the normal level or concentration by a predetermined amount to avoid damaging treated retinal tissue.

2. The process of claim 1, wherein the light beam has a wavelength between 600 nm and 1000 nm and a depth resolution of the order of 3 to 10 microns.

3. The process of claim 1, wherein the light beam is split into a reference beam and a sample beam applied to the retina.

4. The process of claim 3, wherein the detecting step comprises using a photodetector to detect light reflected from the retina.

5. The process of claim 1, wherein an optical coherence tomography device is used to apply the light beam to the retina and detect the interferometric signal or pattern.

6. The process of claim 1, wherein the one or more treatment parameters are adjusted when the change in interferometric signal or pattern is ten percent or greater.

7. The process of claim 1, wherein the one or more treatment parameters are adjusted when the level or concentration of melanin in the retinal pigment epithelium is at least three times greater than the normal level or concentration.

8. The process of claim 4, wherein the determining step comprises calculating a ratio of abnormal retinal pigment epithelium melanin and normal retinal pigment epithelium melanin densities according to the calculation of:

$$[\{N\sigma s + \mu backscat\}RPE / \{2N(\sigma s + \sigma a) + 2\mu backscat\}RPE]times[1-\exp[-2w\{N(\sigma s + \sigma a) + \mu backscat\}RPE]], \text{ wherein}$$

N is the number density of the melanin aggregates that absorb and scatter the light beam;

w is the thickness of the retinal pigment epithelium melanin layer;

σs denotes a cross section of a melanin aggregate for backwards scattering;

σa denotes a cross section of a melanin aggregate for absorption; and

μback scat is a coefficient for backscattering from a structural matrix of the retina.

9. The process of claim 1, wherein the adjusting step comprises adjusting at least one of a retinal spot size of a treatment light beam, a pulse train duration of the treatment light beam, a duty cycle of the treatment light beam, or a power of the treatment light beam.

10. The process of claim 9, wherein the adjusting step comprises increasing a retinal spot size of a treatment light beam.

11. The process of claim 9, wherein the adjusting step comprises lowering a pulse train duration of a treatment light beam.

12. The process of claim 9, wherein the adjusting step comprises lowering a duty cycle of a treatment light beam.

13. The process of claim 9, wherein the adjusting step comprises lowering a power of a treatment light beam.

14. The process of claim 1, including the step of automatically adjusting one or more treatment parameters of a retina therapy system when the concentration of melanin in the retinal pigment epithelium of the eye exceeds the predetermined amount.

15. The process of claim 11, including the step of notifying of the one or more retinal treatment parameters that is adjusted.

16. A process for safely providing retinal phototherapy, comprising the steps of:
generating an interferometric signal or pattern including splitting a light beam having a wavelength between 600 nm and 1000 nm into a reference beam and a sample beam having a depth resolution to the order of 3 to 10 microns applied to a retinal pigment epithelium of an eye;
detecting the interferometric signal or pattern;
determining if a level or concentration of melanin within the retinal pigment epithelium of the retina of the eye is elevated compared to a normal level or concentration using the detected interferometric signal or pattern; and
adjusting one or more treatment parameters of the retinal phototherapy if the level or concentration of melanin in the retinal pigment epithelium of the eye exceeds the normal level or concentration by a predetermined amount so as to avoid damaging treated retinal tissue.

17. The process of claim 16, wherein the detecting step comprises using a photodetector to detect light reflected from the retina.

18. The process of claim 16, wherein an optical coherence tomography device is used to apply the light beam to the retina and detect the interferometric signal or pattern.

19. The process of claim 16, wherein the one or more treatment parameters are adjusted when the change in interferometric signal or pattern is ten percent or greater.

20. The process of claim 16, wherein the one or more treatment parameters are adjusted when the level or concentration of melanin in the retinal pigment epithelium is at least three times greater than the normal level or concentration.

21. The process of claim 17, wherein the adjusting step comprises adjusting at least one of a retinal spot size of a treatment light beam, a pulse train duration of the treatment light beam, a duty cycle of the treatment light beam, or a power of the treatment light beam.

22. The process of claim 21, wherein the determining step comprises calculating a ratio of abnormal retinal pigment epithelium melanin and normal retinal pigment epithelium melanin densities according to the calculation of:

$$[\{N\sigma s + \mu backscat\}RPE / \{2N(\sigma s + \sigma a) + 2\mu backscat\}RPE]times[1-\exp[-2w\{N(\sigma s + \sigma a) + \mu backscat\}RPE]], \text{ wherein}$$

N is the number density of the melanin aggregates that absorb and scatter the light beam;

w is the thickness of the retinal pigment epithelium melanin layer;

σs denotes a cross section of a melanin aggregate for backwards scattering;

σa denotes a cross section of a melanin aggregate for absorption; and

μback scat is a coefficient for backscattering from a structural matrix of the retina.

23. The process of claim 21, wherein the adjusting step comprises increasing a retinal spot size of a treatment light beam.

24. The process of claim 21, wherein the adjusting step comprises lowering a pulse train duration of a treatment light beam.

25. The process of claim 21, wherein the adjusting step comprises lowering a duty cycle of a treatment light beam.

26. The process of claim 21, wherein the adjusting step comprises lowering a power of a treatment light beam.

27. The process of claim 16, including the step of automatically adjusting one or more treatment parameters of a retina therapy system when the concentration of melanin in the retinal pigment epithelium of the eye exceeds the predetermined amount.

28. The process of claim 27, including the step of notifying of the one or more retinal treatment parameters that is adjusted.

* * * * *